(12) United States Patent
Roell

(10) Patent No.: US 7,610,075 B2
(45) Date of Patent: Oct. 27, 2009

(54) METHOD FOR OPERATING A MEDICAL IMAGING DIAGNOSTIC APPARATUS

(75) Inventor: Stefan Roell, Seigendorf (DE)

(73) Assignee: Siemens Aktiengesellschaft, Munich (DE)

( * ) Notice: Subject to any disclaimer, the term of this patent is extended or adjusted under 35 U.S.C. 154(b) by 1374 days.

(21) Appl. No.: 10/313,316

(22) Filed: Dec. 6, 2002

(65) Prior Publication Data

US 2003/0144589 A1 Jul. 31, 2003

(30) Foreign Application Priority Data

Dec. 7, 2001 (DE) ................................ 101 60 075

(51) Int. Cl.
*A61B 5/05* (2006.01)
(52) U.S. Cl. ..................................... 600/410
(58) Field of Classification Search ................. 400/410; 600/407, 410, 415
See application file for complete search history.

(56) References Cited

U.S. PATENT DOCUMENTS

| | | | | |
|---|---|---|---|---|
| 5,584,293 | A * | 12/1996 | Darrow et al. .............. | 600/410 |
| 6,402,693 | B1 * | 6/2002 | Emery ........................ | 600/443 |
| 6,556,855 | B2 * | 4/2003 | Thesen ....................... | 600/419 |
| 2001/0005135 | A1 | 6/2001 | Thesen | |
| 2001/0048306 | A1 | 12/2001 | Mueller et al. | |
| 2002/0198447 | A1 | 12/2002 | Van Muiswinkel et al. | |
| 2003/0016850 | A1* | 1/2003 | Kaufman et al. ............ | 382/128 |

FOREIGN PATENT DOCUMENTS

| | | |
|---|---|---|
| DE | OS 35 41 935 | 6/1987 |
| DE | OS 199 53 308 | 6/2000 |
| DE | OS 199 43 404 | 4/2001 |
| DE | OS 101 18 194 | 12/2002 |
| JP | 7-299061 | 11/1995 |

OTHER PUBLICATIONS

"Bold Magnetic Resonance Imaging in Real Time," Thesen et al. electromedica 68, No. 1 (2000) pp. 45-51.
"Nonrigid Registration: Concepts, Algorithms and Applications," Rueckert, Medical Image Registration, Chapter 13 (2001).

* cited by examiner

*Primary Examiner*—Long V Le
*Assistant Examiner*—Jacqueline Cheng
(74) *Attorney, Agent, or Firm*—Schiff Hardin LLP

(57) ABSTRACT

In a method for the operation of a medical diagnosis apparatus in an examination, a region of an examination subject to be imaged is placed in an imaging volume of the diagnosis apparatus, a first dataset of the region of interest is registered with a first set of operating parameters of the diagnosis apparatus, and the first set of operating parameters and the first dataset are stored. In a follow-up examination wherein the region of interest is again placed in the imaging volume, a follow-up dataset of the region of interest is registered with the apparatus operated with the stored, first set of operating parameters and the follow-up dataset is stored.

9 Claims, 3 Drawing Sheets

METHOD FOR OPERATING A MEDICAL IMAGING DIAGNOSTIC APPARATUS

BACKGROUND OF THE INVENTION

1. Field of the Invention

The present invention is directed to a method for operating an medical imaging diagnostic apparatus.

2. Description of the Prior Art

Medical imaging diagnostic apparatuses include ultrasound devices, X-ray computed tomography devices and magnetic resonance devices. Magnetic resonance technology is a known technique for acquiring images of the inside of the body of an examination subject. In a magnetic resonance apparatus, rapidly switched gradient fields that are generated by a gradient system are superimposed on a static basic magnetic field that is generated by a basic magnet system. The magnetic resonance apparatus also has a radio-frequency system that beams radio-frequency signals into the examination subject for triggering magnetic resonance signals and that picks up the resulting magnetic resonance signals, on the basis of which magnetic resonance images are produced.

In functional magnetic resonance imaging, for example, datasets are registered in a time sequence from the same region of an examination subject to be imaged. Corresponding methods are known for recognizing and correcting differences between the datasets that are the result of a positional change of the imaged region with respect to the apparatus during the time sequence.

One group of methods for determining positional changes from chronologically successively registered datasets is based on a description of an arbitrary rigid body movement in the three-dimensional space by means of six motion parameters, three parameters characterizing translations and three parameters characterizing rotations. The general motion of the rigid body is linearized, for example, by means of a Taylor development of the first order involving all or selected picture elements of two datasets to be compared, the parameters then being able to be determined therefrom, for example using of an iterative method.

In another group of methods for dataset-based acquisition of positional changes, all or specifically selected points of a first dataset described in k-space and of a second dataset that has been generated temporally following the first are compared to one another. These methods are based on the fact that, due to a positional change between the exposure times of the two datasets, translations and/or rotations of the imaged region are reflected in a variation of phase and/or amounts of the data points given a comparison of data points arranged within the two datasets. The navigator echo technique also is an example of a method of this further group.

Further details about functional magnetic resonance imaging and the methods for acquiring and correcting positional changes employed therein are described, for example, in the article by S. Thesen et al., "Funktionelle Magnetresonanztomografie in Echtzeit", electromedica 68 (2000) No. 1, pages 45-52.

Further, methods are known wherein—differing from methods based on rigid bodies—deformations of the region of interest are permitted over the course of the time sequence for determining positional changes from chronologically successively registered datasets. Further details with respect thereto are described, for example, in the book by J. Hajnal et al., *Medical Image Registration,* CRC Press, 2001, chapter 13, "Dave Rueckert: Nonrigid registration. Concepts, Algorithms and Applications".

For monitoring the progress of a therapeutic regimen, it is standard to repeatedly image a region to be monitored in an examination subject by means of successive and temporally spaced image or data acquisitions (examinations) with a medical diagnosis apparatus. The examinations thereby ensue, for example, with a temporal spacing of a few hours or weeks. In an examination temporally following a first examination, an operator of the diagnosis apparatus thereby attempts to position the examination subject in the diagnosis apparatus by means of manual inputs so that the images to be registered optimally correspond to those of the first examination as to positioning within the examination subject. Only a moderate degree of coincidence is achieved by such the manual adjustment. Further, the degree of coincidence is dependent on the operator. Moreover, such manual adjustment is comparatively time-consuming.

SUMMARY OF THE INVENTION

An object of the present invention is to provide an improved method for the operation of a medical diagnosis apparatus that allows fast action in, among other things, the framework of progress monitoring.

This object is achieved in accordance with the invention in a method for the operation of a medical diagnosis apparatus wherein in an examination, a region of an examination subject to be imaged is placed in an imaging volume of the diagnostic apparatus, a first dataset of the region of interest is registered with a first set of operating parameters of the diagnosis apparatus, and the first set of operating parameters and the first dataset are stored, and in a follow-up examination wherein the region of interest is again placed in the imaging volume, a follow-up dataset of the region of interest is registered with the apparatus operated with the stored, first set of operating parameters and the follow-up dataset is stored.

By storing the first set of operating parameters during the examination and employing this stored set of operating parameters for the follow-up examination, images of the region of interest that are registered with coinciding imaging properties can be registered in both examinations and the images are therefore directly comparable to one another with respect thereto. A manual, time-consuming adjustment of the diagnosis apparatus with the aim of registering images during the follow-up examination that have imaging properties corresponding to images of the examination is therefore eliminated in the follow-up examination.

The stored, first set of operating parameters is accessed so that the placement of the region of interest in the imaging volume during the follow-up examination ensues in conformity with the examination. In one embodiment, the examination subject is placed on a support mechanism of the diagnosis apparatus in the follow-up examination in conformity with the preceding examination. For a patient, for example, this means that the patient—corresponding to the data stored in the first set of operating parameters—is to be placed on his/her back and headfirst. Then, a displacement of the support mechanism for positioning the region of interest in the imaging volume is automatically implemented on the basis of data that are stored in the first set of operating parameters, and without an intermediate stop, for example under a laser aiming device that marks the region of interest.

In another embodiment, the patient is arbitrarily placed on the support mechanism within the framework of the established possibilities in the follow-up examination. A camera system acquires the contours of the patient dependent on the manner in which the patient is supported. A displacement of the support mechanism is determined and implemented therefrom in combination with the stored, first set of operating parameters, so that the region of interest is positioned in the imaging volume in the follow-up examination in a way equivalent to the first examination.

In an embodiment, the first dataset and the follow-up dataset are compared to one another in the follow-up examination for determining a positional change of the region of interest with respect to the imaging volume between the examination and the follow-up examination. In the event of a positional change, another follow-up dataset can then be registered in the follow-up examination with a first set of operating parameters that has been suitably modified in view of the positional change, so that images of the examination and of the follow-up examination show the region of interest, and a region of the examination subject deviating from the region of interest is not registered in the images of the follow-up examination as a consequence of a positioning that differs compared to the examination. As a result, the images of the examination and of the follow-up examination are directly comparable to one another not only as to the aforementioned imaging properties but also as to the region of interest of the examination subject. A comparability of the images is therefore maximum, so that, for example, pathological changes can be unambiguously diagnosed as such.

DESCRIPTION OF THE PREFERRED EMBODIMENTS

Figure 1:
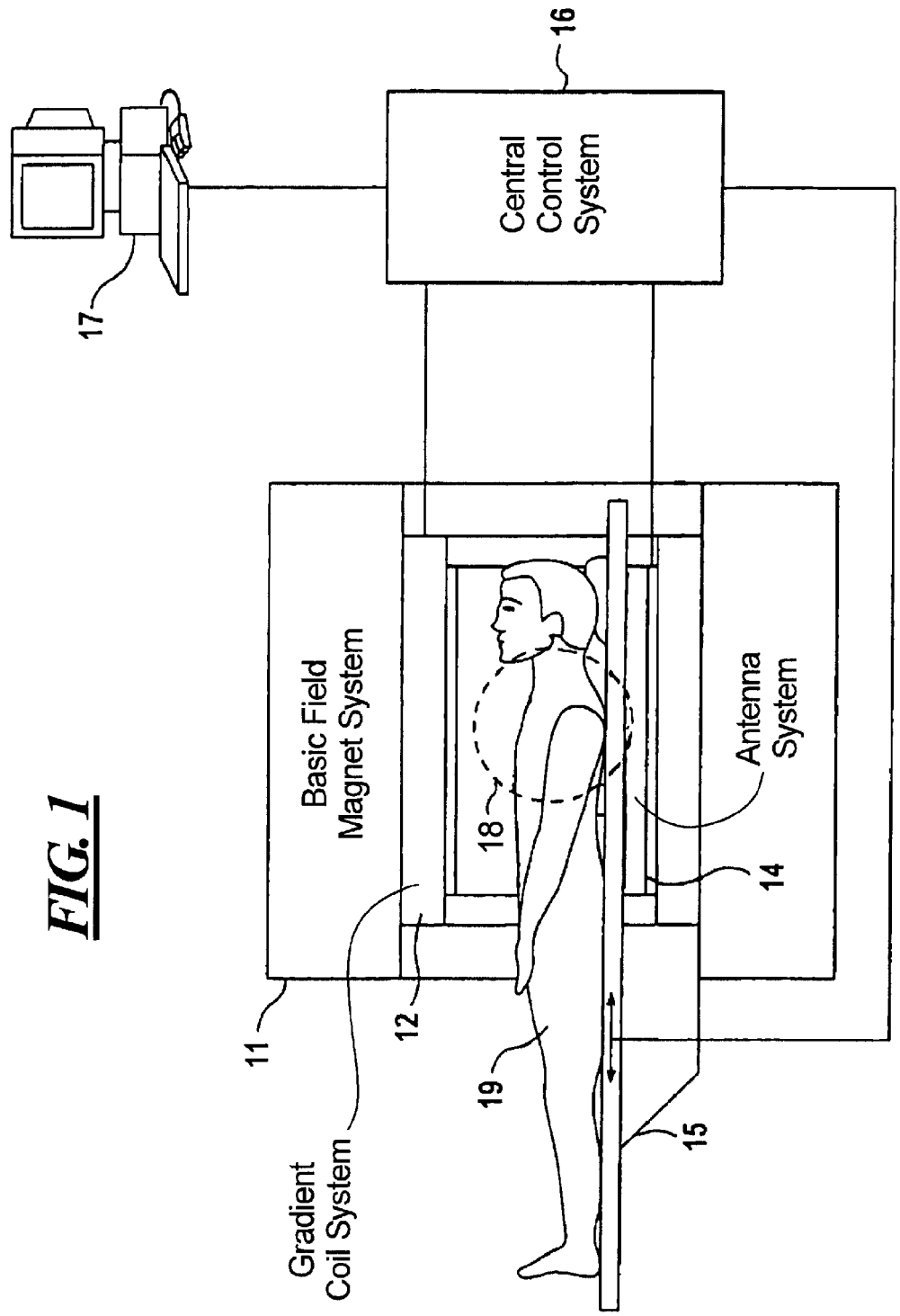
FIG. 1 is a schematic illustration of a magnetic resonance apparatus for implementing the inventive method.

FIG. 1 is a schematic illustration of a magnetic resonance apparatus. The magnetic resonance apparatus has a basic field magnet system 11 for generating a basic magnetic field and a gradient coil system 12 for generating gradient fields. The magnetic resonance apparatus further has an antenna system 14 with which radio-frequency signals can be radiated into an examination subject for triggering magnetic resonance signals and the magnetic resonance signals that are generated can be picked up. The magnetic resonance apparatus also has a displaceable support mechanism 15 on which the examination subject, for example a patient 19 to be examined, is placed.

The gradient coil system 12 is connected to a central control system 16 for controlling currents in the gradient coil system 12. The antenna system 14 is likewise connected to the central control system for controlling the radio-frequency signals to be emitted in conformity with the sequence as well as for the further-processing and storing of the magnetic resonance signals picked up by the antenna system 14. The support mechanism 15 also is connected to the central control system 16 for controlling displacement of the support mechanism 15, for example in order to position a thoracic region of the patient 19 in an imaging volume 18 of the apparatus as region of interest. The central control system 16 is connected to a display and operating device 17 via which inputs of an operator are supplied to the central control system 16, for example the desired sequence type and sequence parameters. Further, the generated magnetic resonance images—among other things—are displayed at the display and operating device 17.

Figure 2:
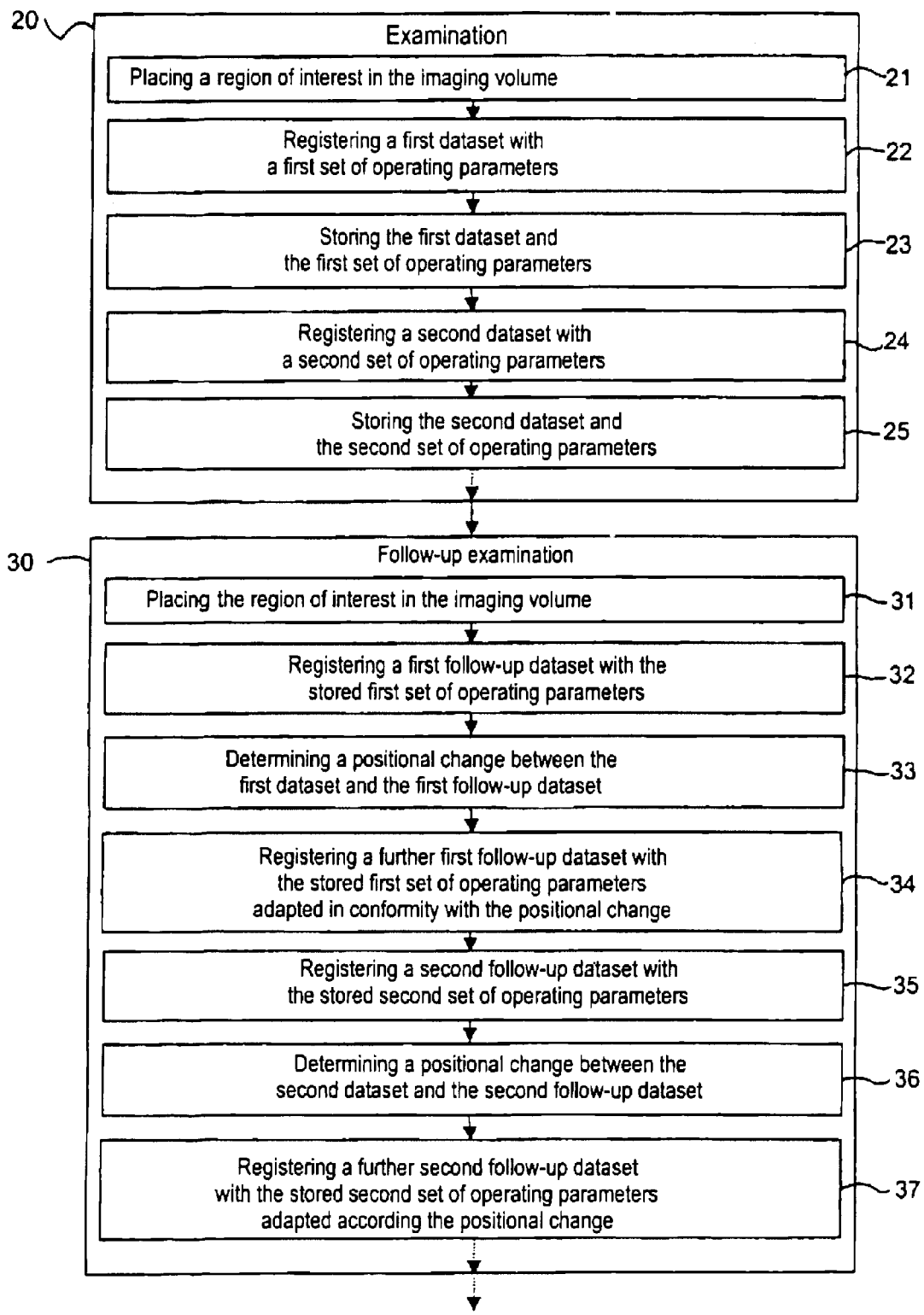
FIG. 2 is a flowchart for a first embodiment of the inventive method for operating a magnetic resonance apparatus.

As an exemplary embodiment, of the invention, FIG. 2 shows a first flowchart for a method for the operation of a magnetic resonance apparatus. The magnetic resonance apparatus shown in FIG. 1 is referenced as an example for explaining the first flowchart.

In an examination 20 of the patient 19, a thoracic region of the patient 19 as region of interest is placed, for example, in the imaging volume 18 of the magnetic resonance apparatus in a first step 21. To that end, the support mechanism 15 together with the patient 19 borne thereon on his/her back is correspondingly displaced. A first dataset, for example a first slice of the region of interest, then is registered in a step 22. A first set of operating parameters is employed for this purpose, this first set combining, for example, data entered by the operator of the magnetic resonance apparatus at the display and operating device 17 such as sequence type, sequence parameters, field of view, resolution, position (attitude) and orientation of the first slice, etc. After the end of the acquisition of the first dataset, this is stored together with the first set of operating parameters in the central control system 16 of the magnetic resonance apparatus in step 23. The first dataset is not necessarily the dataset that is acquired temporally as the first since, for example, the first dataset can be preceded by a scout and/or other magnetic resonance exposures. In a step 24, further, a second dataset, for example a second slice of the thoracic region, is registered upon employment of a second set of operating parameters. The second dataset together with the appertaining second set of operating parameters are also stored in the central control system 16 of the magnetic resonance apparatus in step 25.

The aforementioned datasets are employed, for example, for planning and implementation of a treatment of the thoracic region. After, for example, a few days, the thoracic region of the patient 19 is again examined in the magnetic resonance apparatus in course of a follow-up examination 30 for monitoring the success of a treatment. In the follow-up examination 30, the thoracic region is again placed in the imaging volume 18 in a first step 31. The position in which the patient 19 is to be placed on the support mechanism 15 and what region of the patient 19 is to be positioned in the imaging volume 18 as region of interest can be derived from the stored, first set of operating parameters of the examination 20. It is already known that a perfectly identical positioning with respect to the preceding examination cannot be done due to the fact that the patient 19 cannot be placed on the support mechanism 15 with millimeter precision.

After the positioning of the region of interest in the imaging volume 18, a first follow-up dataset is registered in step 32 using the stored, first set of operating parameters. The first follow-up dataset—due to the employment of the stored, first set of operating parameters—is registered with the same imaging properties such as contrast, resolution, field of view, etc., with respect to the first dataset. This is advantageous not only for the diagnosing physician, who must compare the first data set to the first follow-up dataset, but also for the next step 33. In this step 33, the first dataset is compared to the first follow-up dataset for detecting any positional change of the region of interest with respect to the imaging volume 18 between the examination 20 and the follow-up examination 30. The initially described methods utilized in functional magnetic resonance imaging can be employed for this purpose. In order for a positional change to be detectable, the first dataset and the first follow-up dataset must at least contain the same sub-region of the patient 19. If this is not the case, the method aborts with a corresponding message at the display and, operating device 17. The operator then can implement a correspondingly refined positioning of the region of interest.

A corresponding abort and message also occurs given the initially described methods that allow deformations of the region of interest when the deformations exceed an adjustable threshold.

If a positional change that exceeds a prescribable threshold is detected in step 33, then another follow-up dataset is registered in the following step 34, with the stored, first set of operating parameters being employed in modified form for this purpose so that a coincidence with the first dataset of the examination 20 is achieved not only as to imaging properties but also as to the topicality of the region of interest.

Given a display of both the first dataset as well as the first follow-up dataset at the display and operating device 17, the diagnosing physician can directly compare the two images and identify variations between the examination 20 and the follow-up examination 30 in a simple way, since both the imaging properties as well as the imaged slice are identical in both images.

In the further steps 35 through 37, that set forth above for the steps 32 through 34 is correspondingly repeated for the second set of operating parameters. Corresponding repetitions can follow for further sets of operating parameters.

In a procedure corresponding to the first flowchart of FIG. 1, positional changes that occur between the datasets and one or more follow-up datasets are also advantageously acquired and compensated. In a second flowchart corresponding to FIG. 3 as a further exemplary embodiment of the invention, in contrast, such positional changes are only acquired and compensated with a delay or imprecision of a dataset or follow-up dataset; however, a shorter measurement time for a follow-up examination 30' is advantageously achieved.

Figure 3:
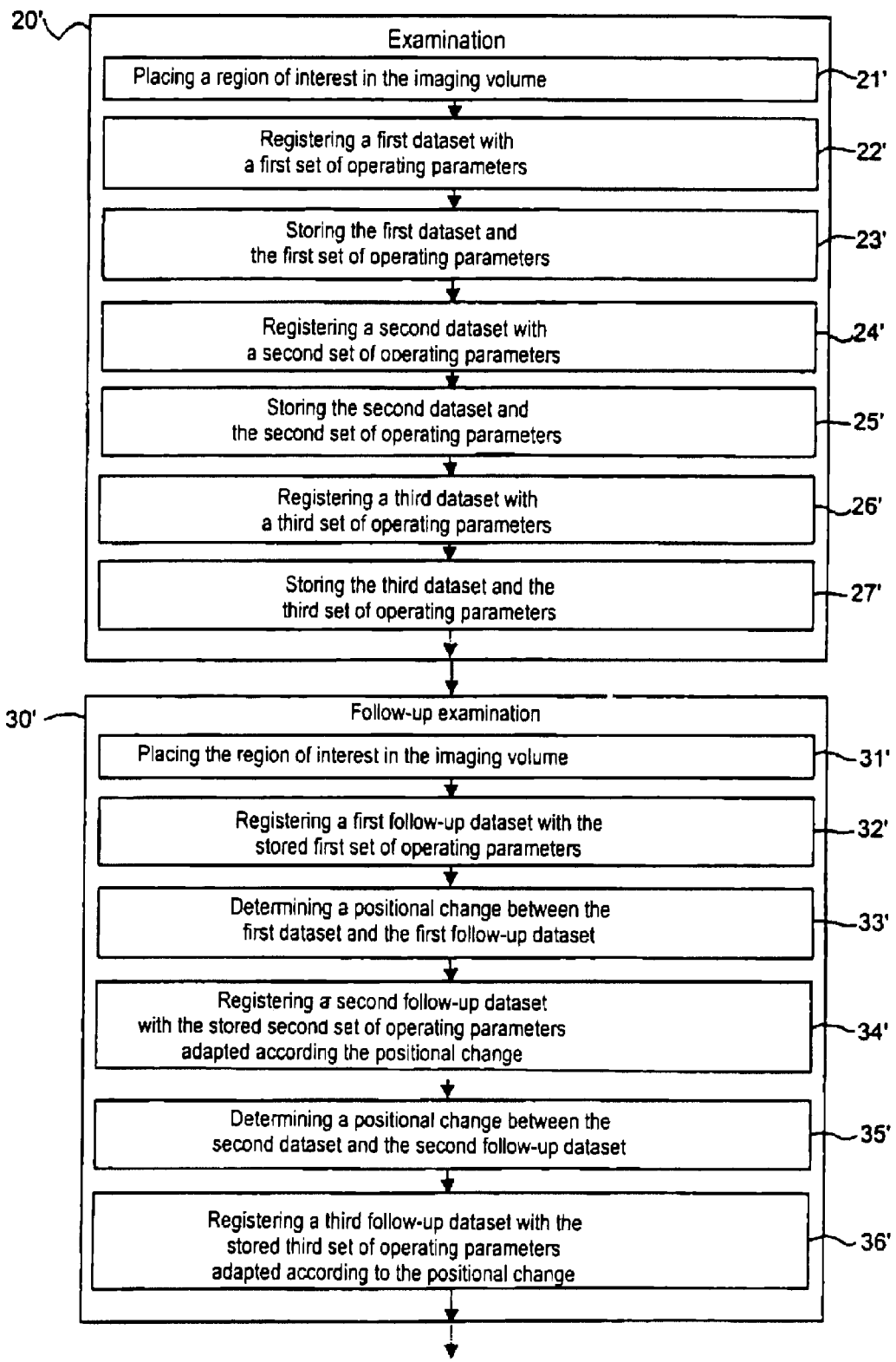
FIG. 3 is a flowchart for a second embodiment of the inventive method for operating a magnetic resonance apparatus.

In the second flowchart of FIG. 3, the first steps 21' through 25' of the examination 20' correspond to the steps 21 through 25 of the examination 20 in the first flowchart of FIG. 2. in the second flowchart, however, a third dataset is additionally registered with a third set of operating parameters in the steps 26' and 27', the third dataset being stored together with the third set of operating parameters.

Steps 31' through 33' of the follow-up examination 30' in the second flowchart of FIG. 3 are also identical to the steps 31 through 33 of the first flowchart of FIG. 2. Following thereupon in a step 34', however, a second follow-up dataset is registered with the stored, second set of operating parameters, which is adapted in conformity with the positional change identified in step 33'. For saving time, the registration of a further follow-up dataset corresponding to step 34 of the first flowchart is foregone. For a corresponding adaptation of the first follow-up dataset, this can be retrospectively corrected as warranted in the second flowchart.

In steps 35' and 36' of the flowchart of FIG. 3, that set forth for the steps 33' through 34' is correspondingly repeated for the third set of operating parameters. Further repetitions for further sets of operating parameters can correspondingly follow.

A further shortening of the time for the follow-up examinations 30 and 30' can be achieved in an embodiment wherein the acquisition of a positional change is implemented only once with the first data set and the follow-up dataset. As a result, however, changes in position that occur after the first dataset and/or the follow-up dataset are left out of consideration.

That set forth for the follow-up examinations 30 and 30' can, of course, be correspondingly applied to every further follow-up examination. Likewise, the method set forth above can also be applied in contrast agent studies, wherein the form of administration, dose, concentration and the time-control of the contrast agent are stored in the sets of operating parameters and can thus be correspondingly reproduced in the follow-up examinations.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for operating a medical diagnostic apparatus comprising the steps of:
    in an examination, placing a region of an examination subject in an imaging volume of a magnetic resonance diagnostic apparatus and obtaining a first dataset of said region of interest by operating said magnetic resonance diagnostic apparatus with a first set of operating parameters, and storing said first set of operating parameters and said first dataset;
    in a follow-up examination, after said examination, again placing said region of interest in said imaging volume of said magnetic resonance diagnostic apparatus, and obtaining a follow-up dataset of said region of interest by operating said magnetic resonance diagnostic apparatus with the stored, first set of operating parameters, and storing said follow-up dataset;
    comparing said first dataset and said follow-up dataset with each other to identify a positional change of said region of interest with respect to said imaging volume between said examination and said follow-up examination; and
    adapting said stored, first set of operating parameters, dependent on said positional change, to obtain an adapted set of operating parameters, and obtaining a further follow-up dataset in said follow-up examination by operating said magnetic resonance diagnostic apparatus with said adapted set of operating parameters.

2. A method as claimed in claim 1 wherein said further follow-up dataset is a first follow-up dataset and wherein said adapted set of operating parameters is a first adapted set of operating parameters, and comprising the additional steps of:
    in said examination, obtaining a second dataset of said region of interest by operating said magnetic resonance diagnostic apparatus with a second set of operating parameters, and storing said second set of operating parameters and said second dataset;
    in said follow-up examination, obtaining a second follow-up dataset of said region of interest by operating said magnetic resonance diagnostic apparatus with the stored, second set of operating parameters;
    comparing said second dataset and said second follow-up dataset to identify a positional change of said region of interest relative to said imaging volume between said examination and said follow-up examination; and
    adapting said stored, second set of operating parameters dependent on said positional change obtained by comparing said second dataset and said second follow-up dataset, to obtain a second adapted set of operating parameters and in said follow-up examination obtaining a further second follow-up dataset of said region of interest by operating said magnetic resonance diagnostic apparatus with said second adopted set of operating parameters.

3. A method as claimed in claim 2 comprising the additional steps of:
    comparing said positional change identified by comparison of said first dataset with said first follow-up dataset to a threshold, and generating said first adapted set of operating parameters if said threshold is exceeded, and comparing the positional change obtained by comparing said second dataset with said second follow-up dataset to said threshold and generating said second adapted set of operating parameters if said threshold is exceeded.

4. A method as claimed in claim 2 comprising obtaining said first follow-up dataset for said region of interest for which said first dataset was obtained, and obtaining said second follow-up dataset for said region of interest for which said second dataset was obtained.

5. A method as claimed in claim 1 wherein said follow-up dataset is a first follow-up dataset and wherein said adapted set of operating parameters is a first adapted set of operating parameters, and comprising the additional steps of:

in said examination, obtaining at least one second dataset of said region of interest with a second set of operating parameters, and storing said second set of operating parameters and said second dataset;

adapting said stored, second set of operating parameters dependent on said positional change, to obtain a second adapted set of operating parameters; and in said follow-up examination, obtaining a second follow-up dataset by operating said magnetic resonance diagnostic apparatus with said second adapted set of operating parameters.

6. A method as claimed in claim 5 comprising the additional steps of:

in said examination, obtaining a third dataset of said region of interest by operating said magnetic resonance diagnostic apparatus with a third set of operating parameters, and storing said third set of operating parameters and said third dataset;

comparing said second dataset with said second follow-up dataset to identify a positional change in said region of interest relative to said imaging volume between said examination and said follow-up examination;

adapting said stored, third set of operating parameters dependent on said positional change identified by comparing said second dataset and said second follow-up dataset to obtain a further adapted set of operating parameters; and in said follow-up examination, obtaining a third follow-up dataset by operating said magnetic resonance diagnostic apparatus with said further adapted set of operating parameters.

7. A method as claimed in claim 6 comprising the additional steps of:

comparing said positional change identified by comparison of said first dataset with said first follow-up dataset to a threshold, and generating said first adapted set of operating parameters if said threshold is exceeded, and comparing the positional change obtained by comparing said second dataset with said second follow-up dataset to said threshold and generating said second adapted set of operating parameters if said threshold is exceeded.

8. A method as claimed in claim 1 comprising obtaining said first follow-up dataset for said region of interest for which said first dataset was obtained, and obtaining said second follow-up dataset for said region of interest for which said second dataset was obtained.

9. A method as claimed in claim 1 comprising aborting said follow-up examination if said comparison between said first dataset and said follow-up dataset is inconclusive regarding said positional change between said examination and said follow-up examination.

* * * * *